(12) United States Patent
Fortuna et al.

(10) Patent No.: US 11,723,607 B2
(45) Date of Patent: *Aug. 15, 2023

(54) RADIOLOGICAL IMAGING DEVICE

(71) Applicant: Epica International, Inc., San Clemente, CA (US)

(72) Inventors: Damiano Fortuna, Rignano Sull'Arno (IT); Leonardo Manetti, Montevarchi (IT); Giulio Raimondi, Pisa (IT); Giovanni De Santis, Pisa (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/008,536

(22) Filed: Aug. 31, 2020

(65) Prior Publication Data

US 2020/0397388 A1 Dec. 24, 2020

Related U.S. Application Data

(63) Continuation of application No. 15/781,117, filed as application No. PCT/IB2016/056955 on Nov. 18, 2016, now Pat. No. 10,758,192.

(30) Foreign Application Priority Data

Dec. 4, 2015 (IT) .......................... UB2015A006291

(51) Int. Cl.
*A61B 6/00* (2006.01)
*A61B 6/03* (2006.01)
(Continued)

(52) U.S. Cl.
CPC ............ *A61B 6/035* (2013.01); *A61B 6/0407* (2013.01); *A61B 6/102* (2013.01); *A61B 6/4241* (2013.01); *A61B 6/4405* (2013.01); *A61B 6/4447* (2013.01)

(58) Field of Classification Search
CPC ....... A61B 6/035; A61B 6/0407; A61B 6/102; A61B 6/4241; A61B 6/4405; A61B 6/4447

See application file for complete search history.

(56) References Cited

U.S. PATENT DOCUMENTS

| | | | |
|---|---|---|---|
| 6,113,264 A * | 9/2000 | Watanabe | A61B 6/466 378/196 |
| 6,619,840 B2 * | 9/2003 | Rasche | A61B 6/032 378/196 |

(Continued)

*Primary Examiner* — Dani Fox
(74) *Attorney, Agent, or Firm* — Steptoe & Johnson LLP; Carl B. Wischhusen

(57) ABSTRACT

A radiological imaging device includes a gantry defining an analysis area configured to contain at least a portion of a patient to be analyzed and a circular extension trajectory extending around a central axis. The gantry includes a source configured to emit radiation, a detector configured to receive the radiation after the radiation has passed through the analysis area, and a casing defining a housing volume for at least the source and the detector. The casing includes a bottom arched module, an arched module mobile with respect to the bottom arched module, and a movement apparatus. The mobile arched module is housed in the bottom arched module and configured to vary the angular extension of the casing and of the housing volume keeping the source and the detector in the housing volume. The movement apparatus, outside the housing volume, is configured to move the arched modules. The radiological imaging device performs at least two of tomography, fluoroscopy, and X-ray.

14 Claims, 5 Drawing Sheets

(51) Int. Cl.
*A61B 6/04* (2006.01)
*A61B 6/10* (2006.01)

(56) References Cited

U.S. PATENT DOCUMENTS

2015/0320370 A1\* 11/2015 Bouvier ................. A61B 6/102
378/189
2016/0038109 A1\* 2/2016 Fortuna ................ A61B 6/4447
378/64

\* cited by examiner

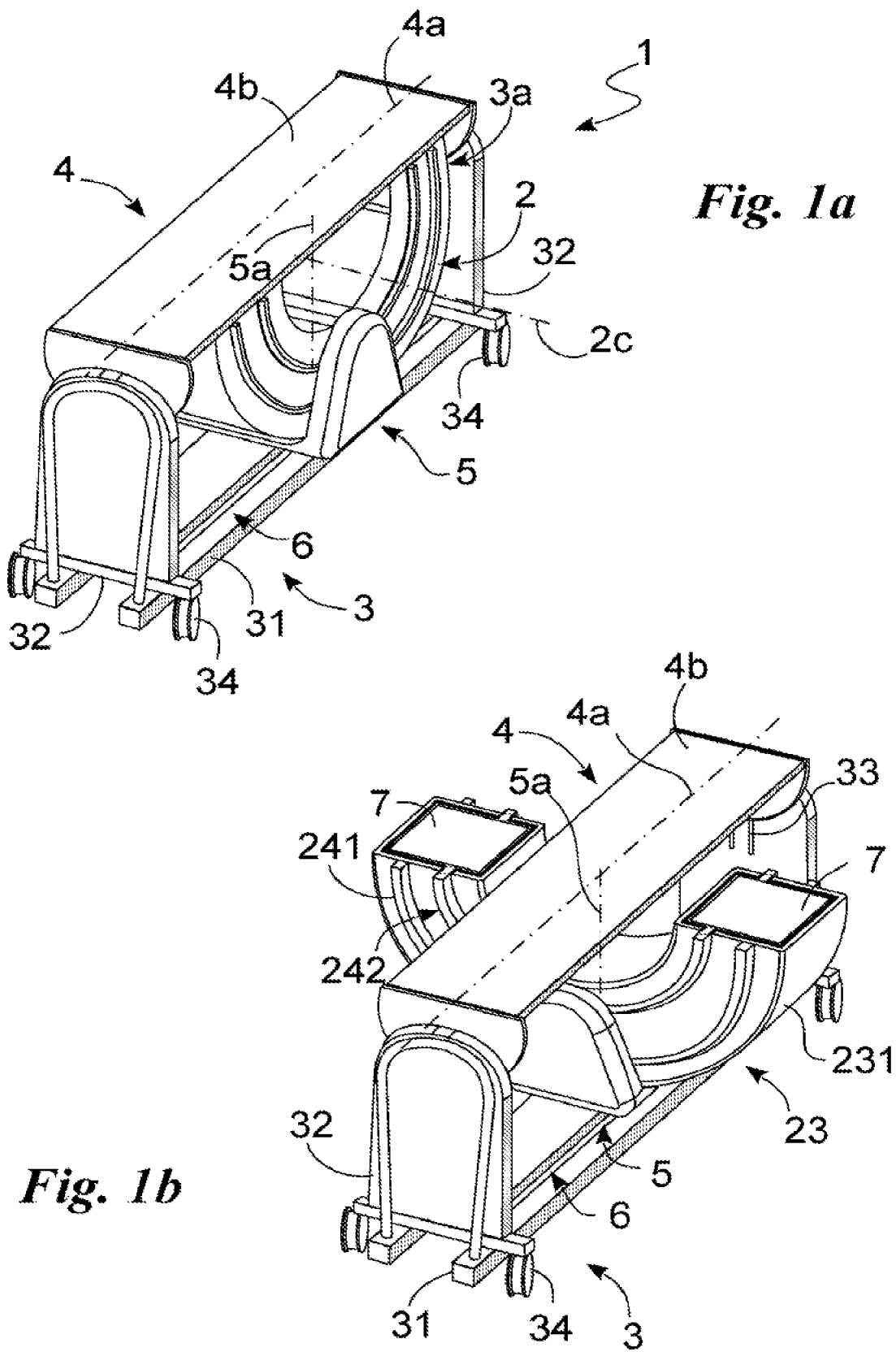

RADIOLOGICAL IMAGING DEVICE

CLAIM OF PRIORITY

This application is a continuation of U.S. application Ser. No. 15/781,117, filed Jun. 1, 2018, now U.S. Pat. No. 10,758,192, which is a National Stage Filing of International Application No. PCT/IB2016/056955, filed Nov. 18, 2016, which claims priority from Italian Patent Application No. UB2015A006291, filed Dec. 4, 2015. This application claims priority from U.S. application Ser. No. 15/781,117, International Application No. PCT/IB2016/056955, and Italian Patent Application No. UB2015A006291, each of which is hereby incorporated by reference in its entirety.

FIELD OF THE INVENTION

The present invention relates to a radiological imaging device. In particular, the invention relates to a device suitable to be used in the medical/veterinary sphere to obtain images of at least a portion of the internal anatomy of a patient, and thus to perform analyses, diagnoses or other assessments of such patient.

BACKGROUND

As is known, X-ray imaging devices currently on the market, regardless of the analysis performed (tomography, X-ray or fluoroscopy) have substantially the same basic structure. This structure provides a bed on which the patient is placed, a control station suitable to control the operation of the device; a gantry, O-shaped, defining a cavity in which the portion to be analysed is inserted and suitable to perform the radiological imaging of the patient; and a support supporting the gantry and the bed and able to mutually translate the bed and gantry. In detail, an X-ray source, a detector which receives the X-rays after they have passed through the bed, and the patient are positioned inside the gantry. Moreover, to perform a scan with different inclinations or a tomography, the radiological device has a rotation member which, by rotating the entire gantry or only the source and detector around the patient, makes it possible to perform scans at different angles.

The prior art mentioned above has several significant drawbacks. A first important drawback is that the radiological imaging devices currently available are particularly bulky. In fact, the gantry, having to contain the source, the detector and the rotation member, is particularly bulky. In fact, it has a diameter at least equal to 1.5 metres and is therefore unable to pass through doors or other accesses present in hospitals.

For this reason, if, for example, radiological imaging is used to check the outcome of an operation, the patient must be taken from the operating table, laid on a hospital bed, moved in the hospital to the room where the radiological imaging device is located, lifted again, and then laid on the bed of the device. This drawback is further increased by the need to make the source and detector rotate by an angular amplitude of at least 360°, which requires the use of complex and laborious rotation members.

One way to resolve these problems is to have the radiological devices developed with a C-shaped gantry, called a "C-arm," which is composed of a solid C-shaped arched body at the ends of which the source and detector are integrally constrained, and a particular rotation member of the entire C-arm.

This solution, although solving in part the disadvantages set out above, has some important drawbacks. In fact, these radiological imaging devices are able to make the source and detector rotate only by a limited angular amplitude of not more than 200°. As a result, during the performance of a tomography, they are able to capture images only at a certain angle and thus perform a reconstruction of a radiographic image of reduced quality that is therefore difficult to read by the physician. As a result, these radiological imaging devices are often designed for a single function, usually only fluoroscopy, and thus have less functional flexibility. Moreover, the limited rotation does not allow the C-arm devices to perform scanning from any angle.

These drawbacks greatly limit the use of devices with a C-arm gantry, thus most of the radiological imaging devices currently in use are those with an O-gantry.

SUMMARY

In this situation the technical purpose of one embodiment of the present invention is to devise a radiological imaging device able to substantially overcome the drawbacks mentioned above. Within the sphere of this technical purpose one important aim of this embodiment is to obtain an imaging device which makes it possible to move the patient easily and, above all, eliminates or reduces the risks to the patient without detracting from the angular scanning amplitude.

In particular, one important purpose of this embodiment of the invention is to provide a radiological imaging device which has reduced dimensions but nevertheless makes it possible to perform scans of angular amplitude equal to at least 360°.

BRIEF DESCRIPTION OF THE DRAWINGS

The various embodiments will now be shown with the following detailed description of an exemplary embodiment, with reference to the attached drawings in which:

FIGS. 1a-1e show, in perspective, a radiological imaging device according to an embodiment of the invention in a possible operating sequence;

DETAILED DESCRIPTION

Figure 1C:
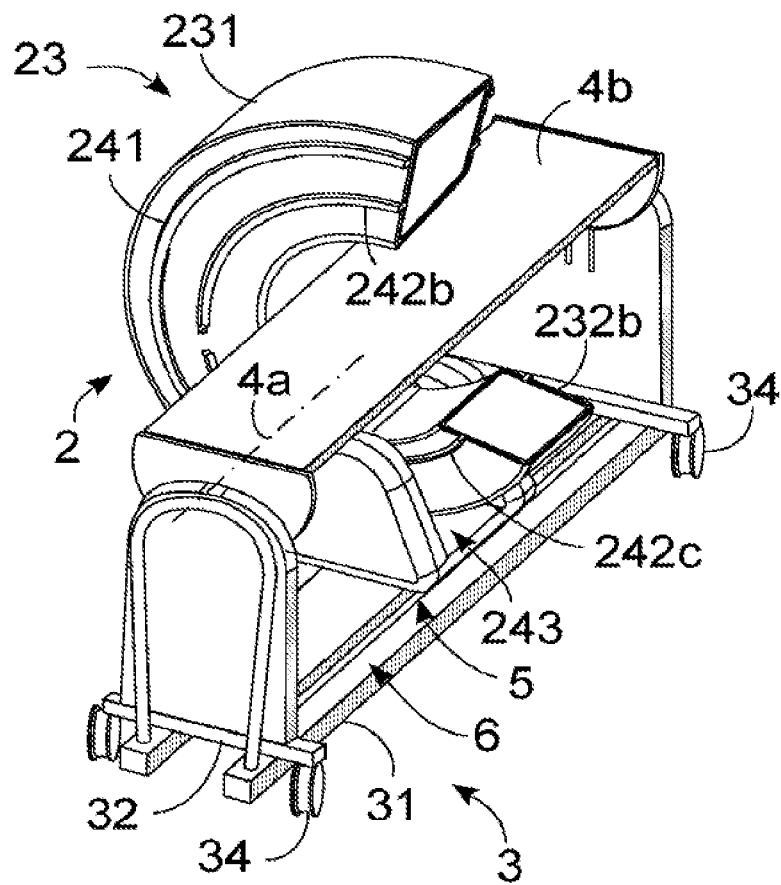

In this document, the measures, values, shapes and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape or geometric reference which it is associated with. For example, these terms, if associated with a value, preferably indicate a divergence of not more than 10% of such value.

In addition, where used terms such as "first", "second", "upper", "lower", "main" and "secondary" do not necessarily refer to an order, a priority relationship or relative position, but may simply be used to more clearly distinguish different components from each other.

Except where specified otherwise, as evidenced by the discussions below, consider that terms such as "processing", "computer", "computing", "evaluation", or the like refer to the action and/or a processes of a computer or calculation system which handles and/or processes data represented as physical, such as electronic magnitudes of logs of a computer system and/or memories of other data similarly represented such as physical quantities inside computer systems, logs or other information storage, transmission or display devices.

With reference to the drawings mentioned, reference numeral 1 globally denotes a radiological imaging device according to an embodiment of the invention. It is suitable for use in the medical (human/veterinary) field for performing radiological imaging of at least one portion of the internal anatomy of a patient. In particular, the radiological imaging device 1 is suitable for use in the medical field (human/veterinary) for performing X-rays, CAT scans, fluoroscopy and other radiological imaging examinations.

The device 1 includes a gantry 2 suitable to perform X-ray imaging and a control unit 1a suitable to manage the operation of the device 1 and, to be precise, at least the gantry 2. The gantry 2 defines an analysis area 2a suitable to contain at least a portion of the patient to be analysed and, appropriately, a circular extension trajectory 2b extending, and thus having its centre, on a central axis 2c.

In the present document the terms "axial", "axially" and similar identify a direction substantially parallel to the central axis 2c, while the terms "radial", "radially" and similar identify a direction substantially perpendicular to the central axis 2c.

The circular extension trajectory 2b lies on a plane substantially perpendicular to the central axis 2c. The gantry 2 includes a source 21 suitable to emit a radiation, preferably X-rays, defining a central propagation axis 21a preferably approximately perpendicular to the central axis 2c; a detector 22 suitable to receive the radiation after it has crossed the analysis area 2a and, therefore, the portion of the patient in analysis; and a casing 23 defining a volume for housing at least the source 21, the detector 22 and extending substantially along the circular extension trajectory 2b.

The source 21 includes an X-ray emitter defining the central axis 21a and, optionally, a tilt-system suitable to rotate, appropriately, with respect to the casing 23, the X-ray emitter and, therefore, the propagation axis 21a, preferably around a tilt-axis approximately parallel to the central axis 2c and, more preferably, passing through the focal spot of the emitter so as to maintain approximately stationary the focal spot.

The detector 22 includes at least one sensor defining a surface sensitive to X-rays and suitable to selectively perform, appropriately on the basis of a command given by the operator, tomographies, fluoroscopies and/or X-rays. It consequently defines at least one sensitive surface suitable to detect the radiation and, in particular, substantially perpendicular to the axis of propagation 21a. The at least one sensor may include at least one of: a linear sensor and, preferably, two linear sensors defining sensitive surfaces substantially coplanar; a rectangular sensor, known as a flat panel, preferably suitable to vary the extension of the active sensitive surface; a direct photon count sensor; a dual energy sensor; a concavity sensor directed towards the central axis 2c; a variable geometry sensor: flat or concave.

The detector 22 may further include at least one lateral and/or vertical movement apparatus and, in detail, at least one waver suitable to translate along a waving axis and a lifting system suitable to move the sensor along a lifting axis approximately perpendicular to the waving axis. The waver presents a slider connected to the sensor, a waving guide defining the waving axis and a motor, in detail electric, controlling the movement of the slider on the waving guide. The waving axis is substantially perpendicular to the central propagation axis 21a and to the central axis 2c. The lifting system includes a linear actuator, preferably electric, suitable to move the sensor and, preferably, the waver along the lifting axis. The lifting axis is approximately parallel to the central axis of propagation 21a and substantially perpendicular to the central axis 2c.

The casing 23 constitutes the outer body of the gantry 2 and, consequently, defines the overall dimensions and, in particular, the angular extension of the gantry 2 and the trajectory 2b. The casing 23 and therefore the gantry 2 are of the telescopic type and, consequently, suitable to vary their angular extension along the extension trajectory 2b preferably defining at least a rest configuration and at least one working configuration for the gantry 2. Advantageously, the casing 23 and therefore the gantry 2 vary their angular extension and, therefore, the angular extension of the housing defined by the casing 23, keeping the source 21 and detector 22 inside the housing volume.

In the rest configuration (FIGS. 1a-1b, 2, 4a) the casing 23 and the gantry 2 are contracted and have a minimum angular extension. Consequently, the casing 23, the gantry 2 and therefore the circular extension trajectory 2b define an arc of circumference substantially centred on the axis 2c and having an angular extension approximately less than 260°. In detail, in the rest configuration the trajectory 2b has a minimum angular extension of angular amplitude approximately less than 210° and, in more detail, substantially equal to 190°.

In one working configuration (FIGS. 1c-1e, 4b), the casing 23 and the gantry 2 have a circular extension trajectory 2b having a greater angular extension than the minimum angular extension so as to at least partially surround at least a major portion of the analysis area 2a allowing the source 21 and the detector 22 to place themselves on opposite sides of the axis 2c and thus the area 2a. In particular, the gantry 2 defines a working configuration of maximum extension (FIGS. 1e, 4b), in which the casing 23 and therefore the gantry 2 are approximately closed and present the circular extension trajectory 2b which presents an angular extension of 360° defining, accordingly, an O-shaped gantry 2 enclosing and, suitably, laterally delimiting the entire analysis area 2a.

Note that gantry 2 passes from one configuration to the other keeping the source 21 and detector 22 always inside the housing volume regardless of the angular extension of the casing 23 and thus of the gantry 2 along the circular extension trajectory 2b, as more fully described below.

Appropriately, in some cases, if the sensor is moved by the lifting system with a stroke of greater amplitude than a predefined threshold, the detector 22 can come out and protrude at least partially from the casing 23. In fact, to allow the lifting system to move the sensor along the lifting axis, the gantry 2 and, in particular, the casing 23 may present a through window which faces the analysis area 2a and allows the detector 22 to protrude from the casing 23 when translated along the lifting axis.

In order to have such configurations, the casing 23 includes at least two substantially hollow modules so as to define the housing volume. The modules have a preferred extension trajectory substantially coinciding with the circular extension trajectory 2*b*, i.e. with the centre on the central axis 2*c*, and, advantageously, different cross-sections allowing for their mutual insertion/overlapping. In detail, the casing 23 includes at least one, preferably only one, bottom arched module 231 and at least one arched module mobile with respect to the bottom arched module 231 so as to vary the angular extension of the casing 23 and of the gantry and, thus, the housing volume. In more detail, the casing 23 includes a bottom arched module 231, a first mobile arched module 232*a* and a second mobile arched module 232*b* placed at the end of the bottom arched module 231 opposite the first module 232*a* and preferably substantially specular to the first module 232*a*.

Mobile modules 232*a* and 232*b*, as described below, are mobile in a dependent manner, i.e. simultaneously and with substantially the same speed and same direction of advancement along the trajectory 2*b*, and independently of each other. The arched modules 231, 232*a* and 232*b* have substantially the same barycentric extension axis preferably approximately coinciding with the circular extension trajectory 2*b*.

In order to have, in the working configuration of maximum extension, an O-shaped gantry 2, the sum of the angular amplitudes of the arched modules 231, 232*a* and 232*b* is at least equal to 360°. Preferably, the sum of the angular amplitudes of the arched modules 231, 232*a* and 232*b* is at least 370° so as to always have an overlap zone of the mobile arched modules 232*a* and 232*b* with the bottom arched module 231 suitable to give greater structural stability to the gantry 2. In particular, the bottom arched module 231 has an angular extension approximately less than 240° and, more particularly, substantially less than 210° and, even more particularly, substantially between 190° and 160°.

Each mobile arched module 232*a* and 232*b* has an angular extension smaller than the angular semi-extension of the bottom module 231 so that, when the radiological imaging device is in the rest configuration, the mobile modules 232*a* and 232*b* are inside the bottom module 231 and spaced apart defining a free sector 231*a* of the bottom module 231. Appropriately, the mobile modules 232*a* and 232*b* preferably have mutually the same angular extension and the free sector 231*a* is appropriately placed in the middle of the bottom body 231, i.e. at the bisector of the angle of extension of the bottom body 231. In particular, each mobile arched module 232*a* and 232*b* has an angular extension approximately less than 140° and, preferably approximately less than 120° and, more preferably, substantially between 90° and 60°.

The mobile arched modules 232*a* and 232*b* have different cross-sections from that of the bottom arched module 231 so as to at least partially overlap the bottom arched module 231 and, advantageously, vary the extension of the part of the mobile module 232*a* and 232*b* overlapping the bottom arched module 231 during a change of configuration. Preferably, the mobile arched modules 232*a* and 232*b* have a cross section less than that of the bottom arched module 231 so as to be housed inside it and, advantageously, vary the extension of the part of the mobile module 232*a* and 232*b* inside the bottom arched module 231 during a change of configuration.

Preferably, in the rest configuration, each mobile arched module 232*a* and 232*b* is totally overlapped and, to be precise, housed in the bottom arched module 231 so that the angular extension of the gantry 2 is substantially equal to that of the bottom arched module 231. More preferably, in the rest configuration the mobile arched modules 232*a* and 232*b* are completely housed in the bottom arched module 231.

In the at least one working configuration, at least one of the mobile arched modules 232*a* and 232*b* and, in particular, each mobile arched module 232*a* and 232*b* protrudes at least partially from the bottom arched module 231 so that the angular extent of the gantry 2 is greater than that of the bottom arched module 231. In detail, in the at least one working configuration, the angular extension of the gantry 2 is approximately equal to the angular extension of the bottom arched module 231 plus the angular extension of each portion of mobile arched module 232*a* and 232*b* protruding from the bottom arched module 231.

Bottom arched module 231, having to contain inside it the mobile modules 232*a* and 232*b*, defines a portion of the housing volume with a cross-section substantially at least equal and in particular, greater than the cross-section of the mobile modules 232*a* and 232*b*. Consequently, the cross-sections of the portion of housing volume of the mobile modules 232*a* and 232*b* are substantially equal to each other and less than the cross-section of the portion of housing volume of the bottom arched module 231. The modules 231, 232*a* and 232*b* are identifiable in hollow, arched profiles. In order to move the at least one mobile arched module 232*a* and/or 232*b* with respect to the bottom arched module 231 and, thus control the passage between the working and rest configurations, the gantry 2 includes a movement apparatus 24 of at least the mobile arched modules 232*a* and/or 232*b* with respect to the bottom arched module 231.

Advantageously, the movement apparatus 24 is suitable to move both the mobile modules 232*a* and 232*b* and the bottom module 231 allowing, in addition to the change of configuration, the source 21 and detector 22 to rotate around the analysis area 2*a* and, thus the central axis 2*c* defining a rotation of maximum amplitude at least equal to 360°.

The apparatus 24 includes at least a bottom guide 241 integral with the bottom arched module 231 and defining a bottom movement trajectory 241*a*, at least one mobile guide 242 integral with the at least one mobile arched module and defining a mobile movement trajectory 242*a*, and at least one thrust assembly 243 suitable to engage at least one of the guides 241 and/or 242 controlling the rotation of the at least one corresponding arched module 231, 232*a* and 232*b* around the central axis 2*c*.

In particular, the mobile guide 242 is integral with both mobile arched modules 232*a* and 232*b*. It is therefore divided into two sectors and includes a first sector 242*b* integral with the first mobile arched module 232*a* and defining a first portion of the mobile trajectory 242*a*; and a second sector 242*c* integral with the second mobile arched module 232*b* and defining a second portion of the mobile trajectory 242*a*.

The guides 241 and 242 are external to the housing volume and, therefore, to the casing 23. Accordingly, the mover 242 is also external to the housing volume and to the casing 23.

The bottom guide 241 is made on at least one of the outer faces of the bottom arched module 231 preferably not facing the analysis area 2*a*. More preferably, it is made on at least one and, in particular, on only one of the outer faces of the bottom arched module 231 approximately perpendicular to the central axis 2*c*.

The mobile guide 242 and, thus, the sectors 242*b* and 242*c* are made on at least one of the outer faces of the mobile arched modules 232*a* and 232*b* suitably not facing the analysis area 2*a*. Preferably, it is made on at least one and, in particular on only one of the external faces of the mobile arched modules 232a and 232b substantially perpendicular to the central axis 2c.

Appropriately, the guides 241 and 242 are made on outer faces of the arched modules 231, 232a and 232b suitable to overlap each other when the mobile modules 232a and 232b are at least partially inside the bottom arched module 231. The guides 241 and 242 and the movement trajectories 241a and 242a are substantially circular and approximately concentric to the axis 2c. Preferably, the mobile guide 242 and the mobile trajectory 242a are distinct from the bottom guide 241 and from the bottom trajectory 241a so that, when the mobile arched module 232a or 232b is moved with respect to the bottom arched module 231, i.e. there is a change of configuration of the gantry 2, the surfaces of the guides 241 and 242 and trajectories 241a and 242a slide reciprocally without touching and appropriately varying the angular extension of the mobile guide 242 overlapped on the bottom guide 241.

The mobile guide 242 and, consequently, the mobile trajectory 242a are separate from the bottom guide 241 and from the bottom trajectory 241a by having a different radius, calculated with respect to the axis 2c or a different position along the central axis 2c, i.e. the lying planes of the trajectories 241a and 242a intersect the central axis 2c in two separate points. Preferably, the mobile guide 242 and the mobile trajectory 242a have a different radius and, in particular, smaller than that of the bottom guide 241 and of the bottom trajectory 241a.

The angular amplitude of the mobile guide 242 and, to be precise, the individual sectors 242b and 242c, added to that of the bottom guide 241, may be approximately more than 360° so that the gantry 2 always has, even in the working configuration at maximum extension, at least one overlapping area between the guides 241 and 242, i.e. an area where both the mobile guide 242 and the bottom guide 241 are present so that the thrust unit 243 is simultaneously engageable to both of the guides 241 and 242.

In detail, the sum of the angular extensions of the guides 241 and 242 and, therefore, of the movement trajectories 241a and 242a is substantially at least equal to 360° and, in more detail, to 380°. To be precise, the bottom guide 241 has an angular extension approximately equal to that of the bottom module 231. In detail, it has approximately an angular extension approximately smaller than 240°, preferably 210° and, more preferably, substantially between 190° and 180°.

The mobile guide 242 has an angular extension approximately less than 240°, preferably 210° and, more preferably, approximately between 190° and 180°. In detail, each sector 242b and 242c has an angular extension equal to that of the respective mobile module 232a and 232b. In more detail, each sector 242b and 242c has an angular extension of less than 140° preferably than 120° and, more preferably, substantially between 100° and 85°.

Figure 3:
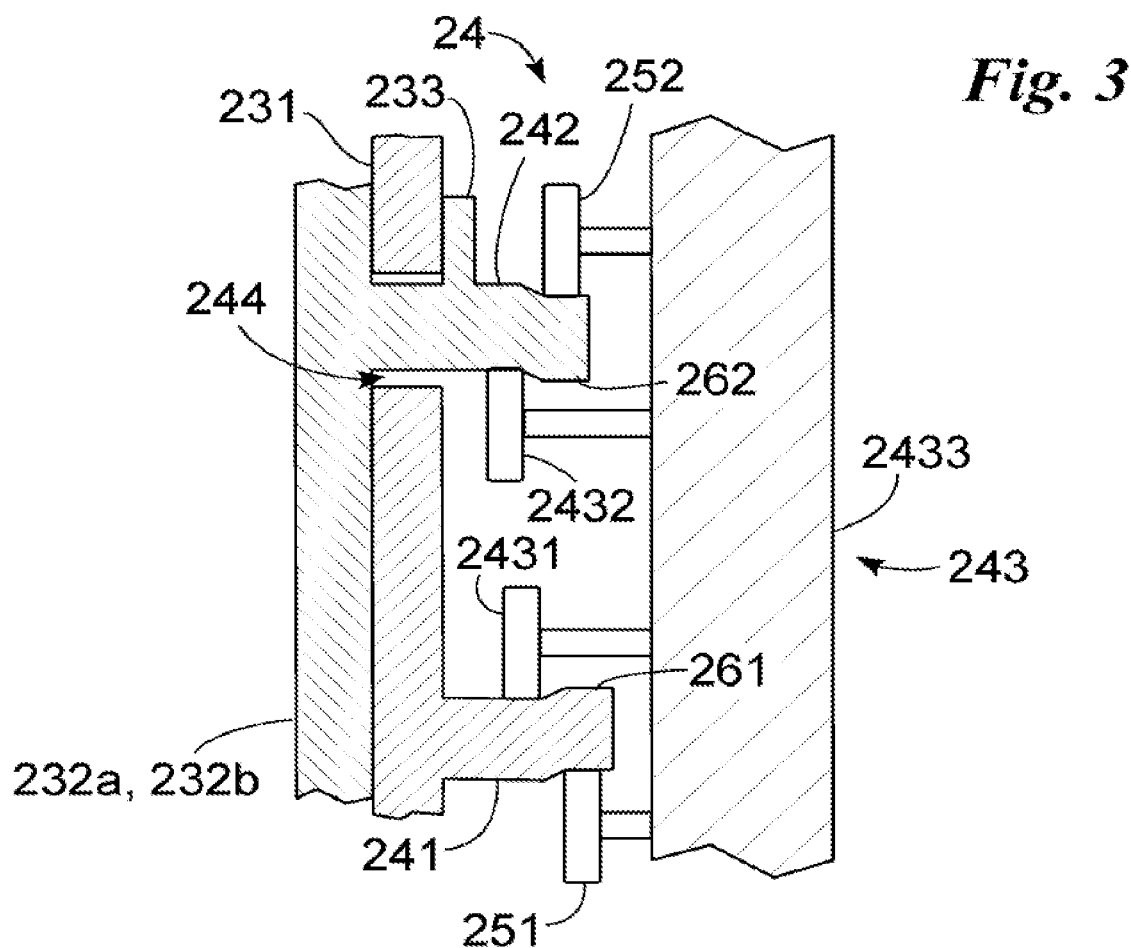
FIG. 3 shows a portion in cross-section of the radiological imaging device.

The thrust assembly 243 is external to the casing 23 and is suitable to engage, individually and/or simultaneously, the guides 241 and 242 controlling the movement of at least part of the arched modules 231, 232a and 232b. As shown in FIG. 3, it includes at least a first engagement element 2431 to the bottom guide 241 suitable to control the rotation of at least the bottom arched module 231; at least one second engagement element 2432 to the mobile guide 242 suitable to control the rotation of at least one mobile arched module 232a or 232b; and, suitably, a support 2433 for elements 2431 and 2432. In order to allow the thrust assembly 243 to always be in contact with at least one of the guides 241 and 242, the at least first engagement element 2431 and/or the at least second engagement element 2432 may respectively define a first engagement area 2431a and a second engagement area 2432a at least partially overlapping one another radially, i.e. along a first approximately radial direction, suitably a circular extension trajectory 2b, and having a suitable angular amplitude. The radial overlap identifies the fact that the engagement areas 2431a and 2432a, if projected on one another in the radial direction, have a non-null overlap. Each engagement area 2431a and 2432a is identifiable in the surface of the element 2431 or 2432 suitable to come into contact with the respective guide 241 or 242. In particular, in the case of several elements 2431 and/or 2432, it is identifiable in the arch enclosed between the areas of several external elements 2431 or 2432 suitable to come into contact with the respective guide 241 or 242.

Preferably, the thrust assembly 243 includes several first engagement elements 2431 mutually angularly spaced along the circular extension trajectory 2b so as to engage to the bottom guide 241 in different points and, thus, have a broader first engagement area 2431a. In detail, the first engagement elements 2431 have a mutual angular distance and, therefore, an amplitude of the first engagement area 2431a substantially at least equal to 10° and, to be precise, substantially between 10° and 30°.

The first engagement element 2431 is identifiable in a toothed wheel, motorised, suitably electrically, and the bottom guide 241 is identifiable in a rack. Alternatively, the bottom guide 241 is substantially smooth and, suitably, the first element 2431 is identifiable in a friction wheel (i.e. suitably coated or made of rubber or other high friction material) motorised, preferably, electrically, i.e. a wheel suitable to engage to the bottom guide 241 and to exploit the friction force between the wheel and the bottom guide 241 to move the bottom module 231.

Appropriately, the thrust assembly 243 includes several second engagement elements 2432 mutually angularly spaced along the circular extension trajectory 2b so as to engage to the mobile guide 242 in different points and, thus, have a broader second engagement area 2432a. In detail, the second engagement elements 2432 have a mutual angular distance and, therefore, an amplitude of the second engagement area 2432a at least equal to 10° and, to be precise, substantially between 10° and 30°. Each second engagement element 2432 is identifiable in at least one toothed wheel, motorised, suitably electrically, and the mobile guide 242 is identifiable in a rack. Alternatively, the mobile guide 242 is approximately smooth and, suitably, coated in rubber or other high friction material and the second element 2432 is a friction wheel, motorised, preferably electrically.

Lastly, to allow the second engagement element of the 2432 to engage to the mobile guide 242 even when the mobile module 232a and/or 232b is inside the bottom arched module 231 the movement apparatus 24 includes at least one through slot 244 made on the bottom arched module 231 and suitable to overlap the mobile guide 242 so as to appropriately put it into view through bottom arched module 231 allowing an engagement between the second thrust means 2432, external to the casing 23, and the mobile guide 242 constrained to the mobile modules 232a and 232b, i.e. inside the casing 23. In particular, the movement apparatus 24 includes a single through slot 244 having an angular extension substantially equal to that of the bottom arched module 231 and extending substantially along the second trajectory 242a. Alternatively, it includes two through slots 244 (FIG. 4b) of which one having an angular extension approximately equal to the first sector 242b and the other having an angular extension approximately equal to the second sector 242c.

Additionally, the movement apparatus 24, to allow the modules 231, 232a and 232b to rotate mutually exclusively, may include at least one of: a radial constraint suitable to prevent a relative radial motion between the thrust assembly 243 and guides 241 and 242; and an axial constraint suitable to prevent a relative axial motion between the thrust assembly 243 and the guides 241 and 242. Appropriately, the movement apparatus 24 includes both the radial constraint and the axial constraint. The radial constraint, shown in FIG. 3, includes at least a first abutment 251 suitable to engage to the bottom guide 241 on the opposite side to the first engagement element 2431 and at least a second abutment 252 suitable to engage the mobile guide 242 on the side opposite the second element 2432. The abutments 251 and 252 are identified in the wheels, preferably idle, toothed or friction. The axial constraint, shown in FIG. 3, includes a first prominence 261 protruding radially from the bottom guide 241 and distal from the bottom module 231 so as to enclose the first engagement element 2431 between first prominence 261 and the bottom module 231 and a second prominence 262 protruding radially from the mobile guide 242 and distal from the mobile module 232a and 232b and in particular from the bottom module 231 so as to enclose the first engagement element 2431 between second prominence 262 and the bottom module 231.

In order to stably reciprocally lock the arched modules 231, 232a and 232b in any position with respect to the bottom arched module 231 and, thus, the gantry 2 in any configuration, the gantry 2 includes at least one lock, placed appropriately in the housing volume, suitable to selectively lock or prevent the relative sliding between arched modules 231, 232a and 232b and, thus, to define a locked position in which it prevents the relative movement between the modules 231, 232a and 232b and a release position in which it allows the relative movement between the modules 231, 232a and 232b. In particular, the gantry includes a first lock suitable to stably constrain the first mobile module 232a to the bottom arched module 231 and a second lock suitable to stably constrain the second module 232b to the bottom arched module 231.

To be precise, the first lock defines a first locking position in which it prevents the relative movement between the first mobile arched module 232a and the bottom arched module 231 and a first release position in which it allows the relative movement between the first mobile arched module 232a and the bottom arched module 231. The second lock defines a second locking position in which it prevents the relative movement between the second mobile module 232b and the bottom arched module 231 and a second release position in which it allows the relative movement between the second mobile arched module 232b and the bottom arched module 231.

Each lock is identifiable in a linear actuator integral with the mobile module 232a and 232b defining a high friction contact surface with the bottom module 231 and suitable to vary its own length, suitably along a substantially radial direction with respect to the circular trajectory 2b so that, in the locked position, the contact surface presses against the bottom module 231 mutually stably constraining the modules 231, 232a and 232b, while in the release position the contact surface is moved away from the bottom module 231 allowing a mutual sliding between these modules.

Lastly, the gantry 2 and, in particular, the casing 23 include means of constraint 233 between the arched modules suitable to allow the modules to approximately exclusively slide substantially along the circular extension trajectory 2b. The means of constraint 233 are consequently suitable to prevent relative radial and axial movements between the arched modules 231, 232a and 232b. They include at least one circular engagement flap extending substantially along at least a portion of the through slot 244 modules so as to reciprocally engage the modules 231, 232a and 232b.

In particular, the means of constraint 233 include, for each mobile arched module 232a and 232b, at least one circular flap protruding axially and externally from the mobile module so as to abut the bottom arched module 231 at the through slot 244. More specifically, the means of constraint 233 include, for each mobile arched module 232a and 232b, two circular flaps suitable to abut opposite sides of the through slot 244. Preferably, a circular flap has a first portion protruding axially from the mobile arched module 232a and 232b through the slot 244 and a second portion protruding radially from the first portion and, in detail, distal from the mobile arched module 232a and 232b and perpendicular to the first portion so as to enclose the bottom arched module 231 between the second portion and a mobile arched module 232a and 232b.

The gantry 2 is suitable to vary its angular extension maintaining, appropriately always, the source 21 and the detector 22 inside the housing volume regardless of the angular extension of the casing 23. It may consequently include at least a support suitable to constrain the source 21 and the detector 22 to the casing 23 and, specifically, inside the housing volume. Specifically, the support is suitable to constrain the source 21 and the detector 22 to at least one arched module 231, 232a and 232b.

To allow the device 1 to pass from the rest configuration to the working configuration placing the source 21 opposite the detector 22 with respect to the central axis 2c, the gantry 2 includes a first support 27 for the source 21 and a second support 28 for the detector 22. Specifically, the first support 27 is suitable to stably constrain the source 21 to one between the bottom arched module 231 and a mobile module 232a or 232b; the second support 28 is suitable to stably constrain the detector 21 to one between a mobile module 232a or 232b and the bottom mobile 231. More specifically, the first support 27 and second support 28 are suitable to stably constrain the source 21 and the detector 22 respectively to a bottom arched module 231 and to a mobile module 232a or 232b.

Figure 4A:
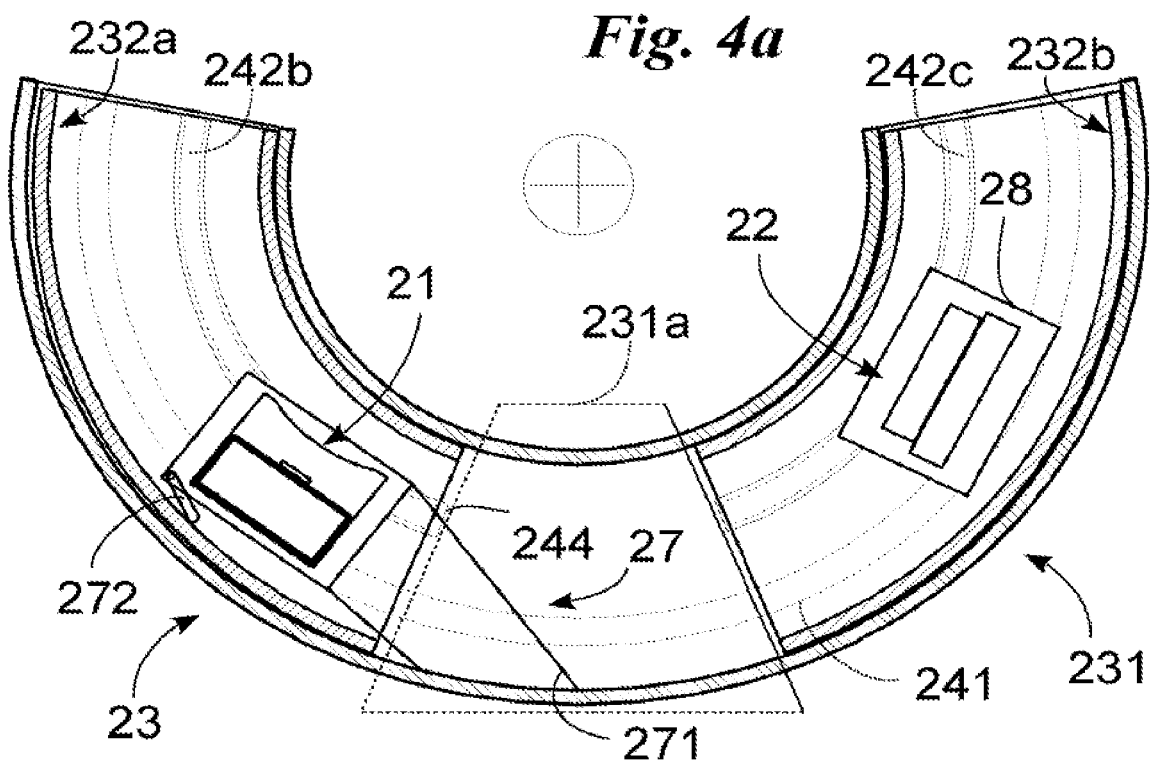
FIGS. 4a-4b show, in cross-section, an assembly of the radiological imaging device according to embodiments of the invention in different configurations.
Figure 4B:
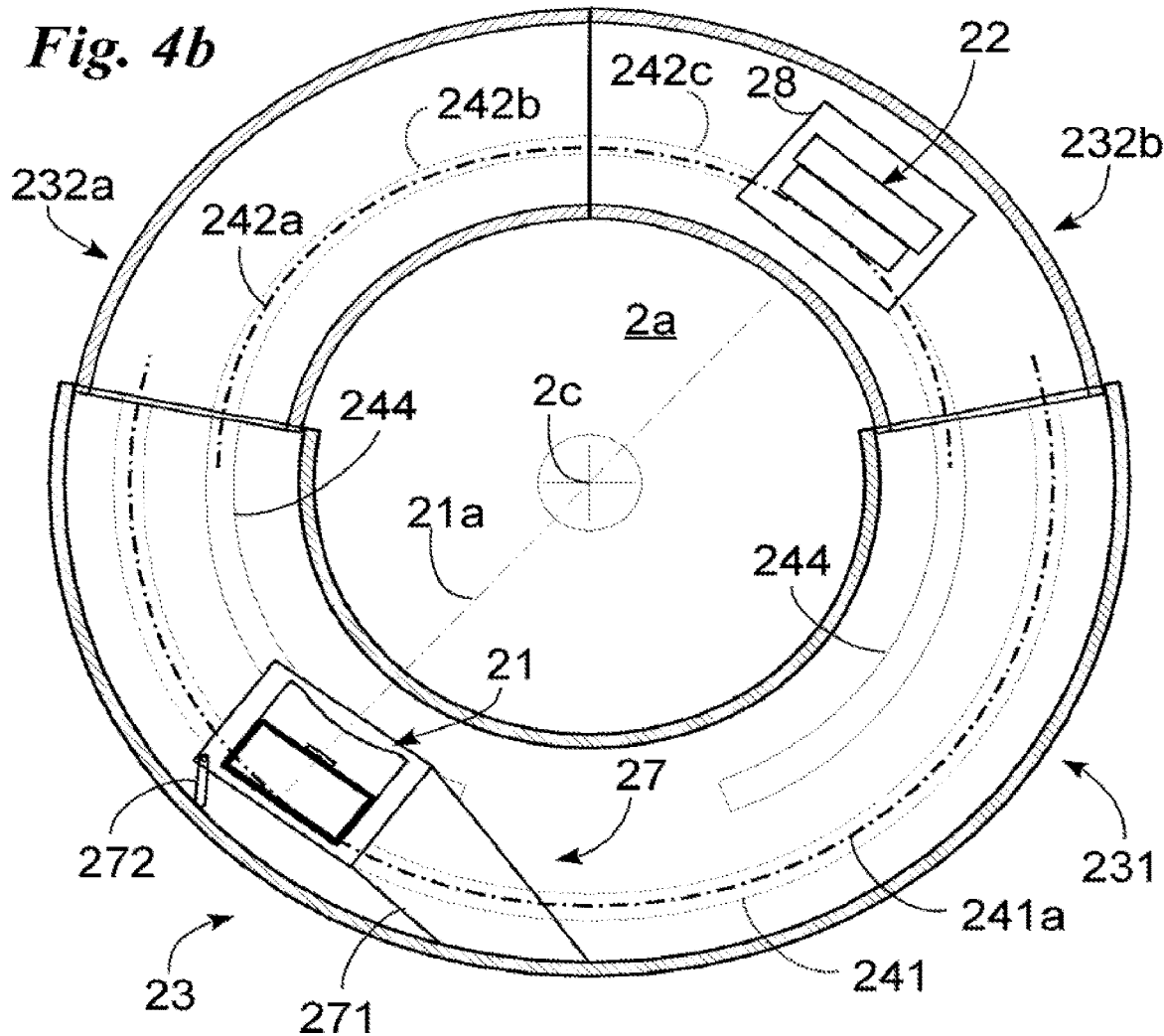
Figure 5:
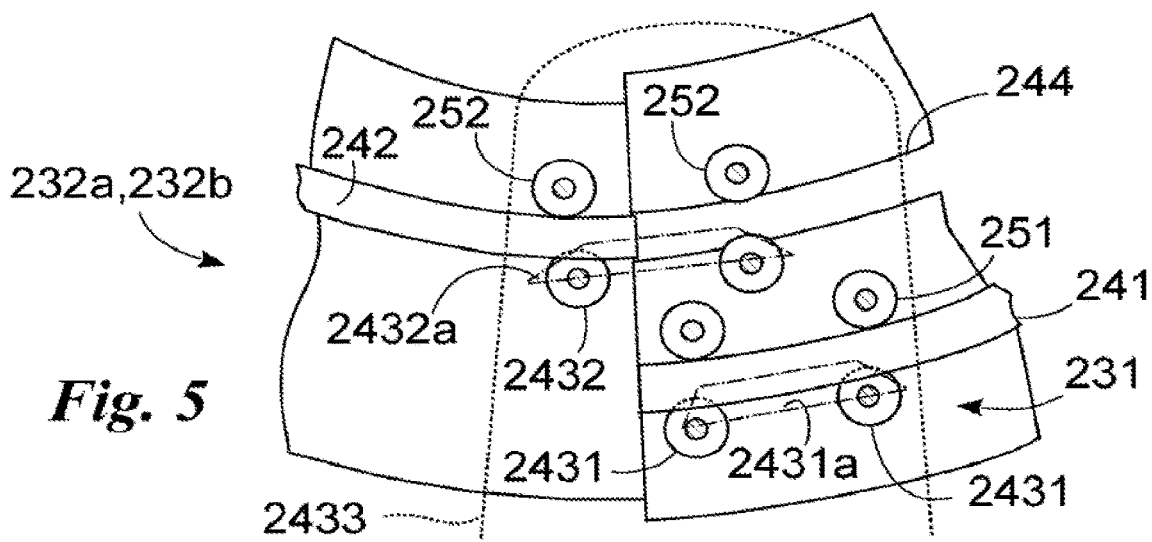
FIG. 5 shows a portion of the radiological imaging device.

In order to allow the passage into the rest configuration, the first support 27 is suitable to constrain the source 21 to the bottom arched module cantilevered, i.e. not in contact with any inner surface of the bottom arched module 231 so that a mobile module is able to position itself between the source 21 and the bottom arched module 231. To such purpose, the first support 27, as shown in FIGS. 4a and 4b, includes a prop 271 integral with the bottom arched module 231 and suitable to support the source 21 cantilevered so as to allow a mobile arched module 232a or 232b to position itself between the source 21 and the bottom arched module 231; and, appropriately, at least one retractable foot 272 suitable to rest on a module 231, 232a and 232b and to support the source 21 on the distal side and, in detail, opposite the prop 271 and, more specifically, to the anchor point of the prop 271 to the bottom arched module 231 (i.e. at the cantilever end of the prop 271 and/or source 21 and thus, at greater distance from the bottom arched module 231 as shown in FIG. 4b).

The prop 271 is constrained to the bottom arched module 231 at the free sector 231a so as not to interfere with the mobile modules 232a and 232b preventing the passage into the rest configuration. The retractable foot 272 is suitable to rest on the bottom arched module 231 at least in the fully extended configuration and on a mobile arched portion 232a and 232b at least in the rest configuration. It includes a stand 2721 hinged to the source 21 and elastic means 2722, appropriately a compression spring, suitable to retract the stand 2721 with respect to the source 21. Optionally, the second support 28 may include a carriage for the detector 22 and a rail integral with the second mobile module 232b and suitable to define, for the carriage, a circular trajectory preferably substantially coincident with the trajectory 2b. Alternatively, the first support 27 is suitable to constrain the source 21 to the first mobile arched module 232a and the second support 28 is suitable to constrain the detector 22 to the second mobile arched module 232b.

In this case, in order to allow the positioning of the source 21 and the detector 22 on opposite sides of the central axis, the first support 27 may include a first slider integral with the source 21 and a first rail integral with the first module 232a and suitable to define, for the first slider, a first circular sliding trajectory approximately coincidental with the extension trajectory 2b; and the second support 28 may include a second slider integral with the detector 22 and a second rail integral with the second mobile module 232b and suitable to define, for the second slider, a second circular sliding trajectory preferably substantially coincident with the trajectory 2b. These rails define for the relative sliders a stroke of substantially at least 10° and, in particular, substantially between 30° and 50°. In particular, these rails are suitable to place at least one between the source 21 and detector 22 cantilevered with respect to the relevant mobile module 232a and 232b so as allow the source 21 and the detector 22 to be on opposite sides with respect to the central axis 2c. The control unit 1a is connected to the other components of the device 1 by a wire 1b and/or via a wireless connection. It is suitable to control and command at least the gantry 2 and its movements. The unit 1a includes a control card able to automatically monitor and control the radiological imaging device 1; and interface components (touch-screen, keyboard, etc.) suitable to enable the operator to control the imaging device 1. In particular, the control unit 1a is suitable to control the operation of the thrust assembly 243 so as to define if and which module 231, 232a and 232b to move. Appropriately, the control unit 1a is suitable to control the operation of at least one lock and, specifically, their passage between the locked position and release position. More particularly, the control unit 1a, placing the locks in the locked position causes the thrust assembly 243 to rotate the entire gantry 2 and placing at least one of the locks in the release position, makes the thrust assembly 243 perform a relative movement between at least one mobile module 232a and 232b with respect to the bottom module 231 and thus a change of configuration of the gantry 2.

In addition to the gantry 2 and to the unit 1a, the radiological imaging device 1 may include a bearing structure 3 suitable to support and move the gantry 2 and defining a free chamber 3a for the gantry 2; and in some cases, a bed 4 suitable to be at least partially inserted in the area of analysis 2a and defining a longitudinal axis 4a and a support surface 4b for the patient. The support surface 4b is substantially parallel to the central axis 2c and is suitable to position itself approximately parallel to the support surface of the imaging device 1. The bearing structure 3 includes a base 31 suitable to support the gantry 2; at least one column 32 suitable to sustain it in a raised position with respect to the base 31, the bed 4; and, in some cases, 33 actuators suitable to move the bed 4 with respect to the base 31.

Optionally, the radiological imaging device is portable and therefore the structure 3 may include movement means 34 of the device 1, preferably castor wheels, suitable to position themselves between the ground and base 31 enabling the movement of the device 1. The base 31 and at least one column 32 define the chamber 3a. In detail, the chamber 3a is defined underneath, i.e. in the vicinity of the floor, by the base 31; along a lateral side of the column 32; if present, along a second lateral side opposite the first side of the second column 32; and optionally above the bed 4. The free chamber 3a has two open cross-sections for access to said chamber extending substantially parallel to the central axis 2c and, in particular, approximately perpendicular to the support surface 4b.

The actuators 33 are placed between the bed 4 and each column 32 so as to change the extension of the chamber 3a by means of an approximately transverse translation and in particular perpendicular to the support surface 4b or, alternatively, independent of each other so to tilt the surface 4b with respect to the gantry axis. Alternatively, the actuators 33 modify the inner chamber 3a by means of a rotation of the bed 2 around an axis substantially parallel to the central axis 2c.

Positioned between the base 31 and the gantry 2, the radiological imaging device 1 has rotation means 5 defining an axis of rotation 5a of the gantry 2; and translation means 6 defining a translation axis 6a of the gantry 2. The translation means 6 are placed between the base 31 and the gantry 2 and include a linear guide 61, preferably motorised, suitable to control the translation along the translation axis 6a; and a translation element 62 joined to the gantry 2, in particular to the thrust assembly 243 and, more specifically, to the support 2433 and suitable to slide along the linear guide 61 thereby translating said gantry 2. The translation axis 6a is substantially parallel to the central axis 2c.

The means of rotation 5 are positioned between the translation means 6 and the gantry 2 with respect to a rotation axis 5a substantially transverse to the axis 2c and, appropriately, to the support surface 4b so as to vary the mutual inclination between the axes 2c and 4a. The means of rotation 5 include a fixed plate 51 suitable to be joined to the translation element 62; a mobile plate constrained to the casing 23 and, to be precise, identifiable in the support 2433; pins, bearings or other similar elements defining the rotation axis 5a; and a control lever 52 suitable to be gripped by the operator and, thus, allow the operator to manually control the rotation around the rotation axis 5a, of the mobile plate and thus of the gantry 2 with respect to the fixed plate 51. The control lever 52 is suitable to be associated with the holes on the plates 51 and thus define, for the gantry 2, a first rotational locked position wherein the central axis 2c is substantially parallel to the longitudinal axis 4a, the trajectory 2b lies on a plane substantially perpendicular to the longitudinal axis 4a; and a second rotational locked position wherein the central axis 2c is approximately perpendicular to the longitudinal axis 4a and the extension trajectory 2b lies in a plane approximately parallel to the longitudinal axis 4a. In addition, the lever 52 defines a third rotational locked position wherein the central axis 2a is substantially parallel to the longitudinal axis 4a, the extension trajectory 2b lies on a plane approximately perpendicular to the longitudinal axis 4a, but the gantry 2 is rotated by 180° with respect to the first position. As an alternative to the lever 52, the rotation means 5 provide a motor suitable to control the aforesaid rotation of the gantry 2 and to define the first and second rotational locked positions and, if necessary, the third position.

Lastly, the imaging device 1 includes one or more cover blocks 7, preferably two, suitable to seal the ends of the casing 23 and in particular the mobile arched modules 232a and 232b.

The functioning of the radiological imaging device, described above in a structural sense, is as follows. Initially, the radiological imaging device 1 is in the rest configuration, i.e. with the gantry 2 placed inside the free chamber 3a and, therefore, the support surface 4b is approximately completely free and substantially accessible from any point. In such rest configuration, the gantry 2 has the casing 23 with the mobile arched modules 232a and 232b, the source 21 and the detector 22 housed in the bottom arched module 231.

Figure 1D:
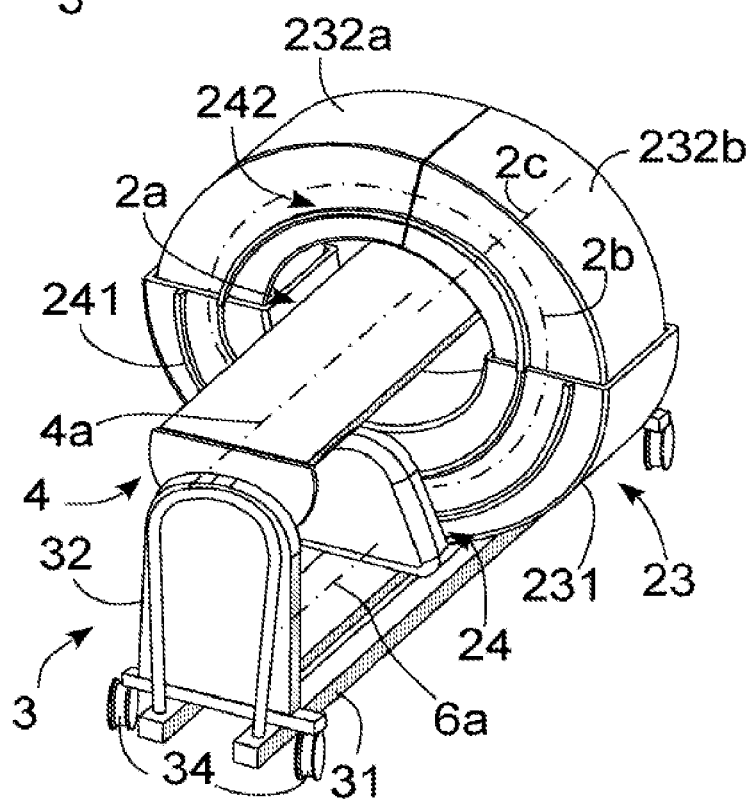
Figure 1E:
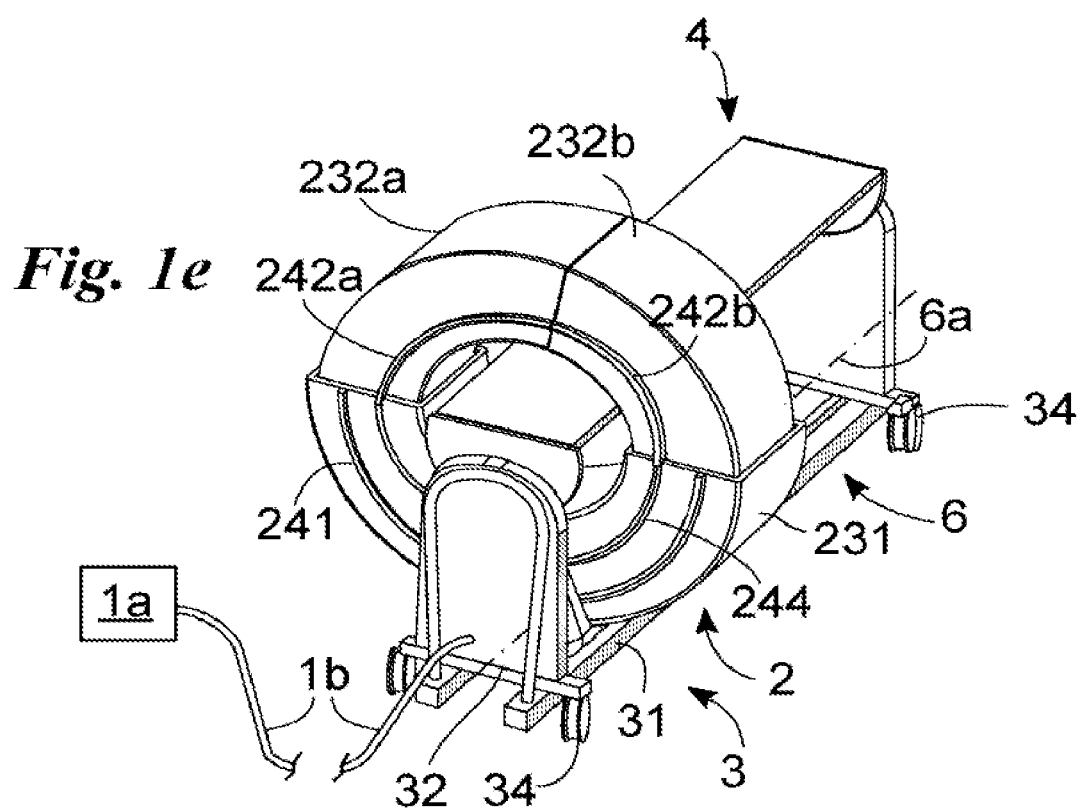
Figure 2:
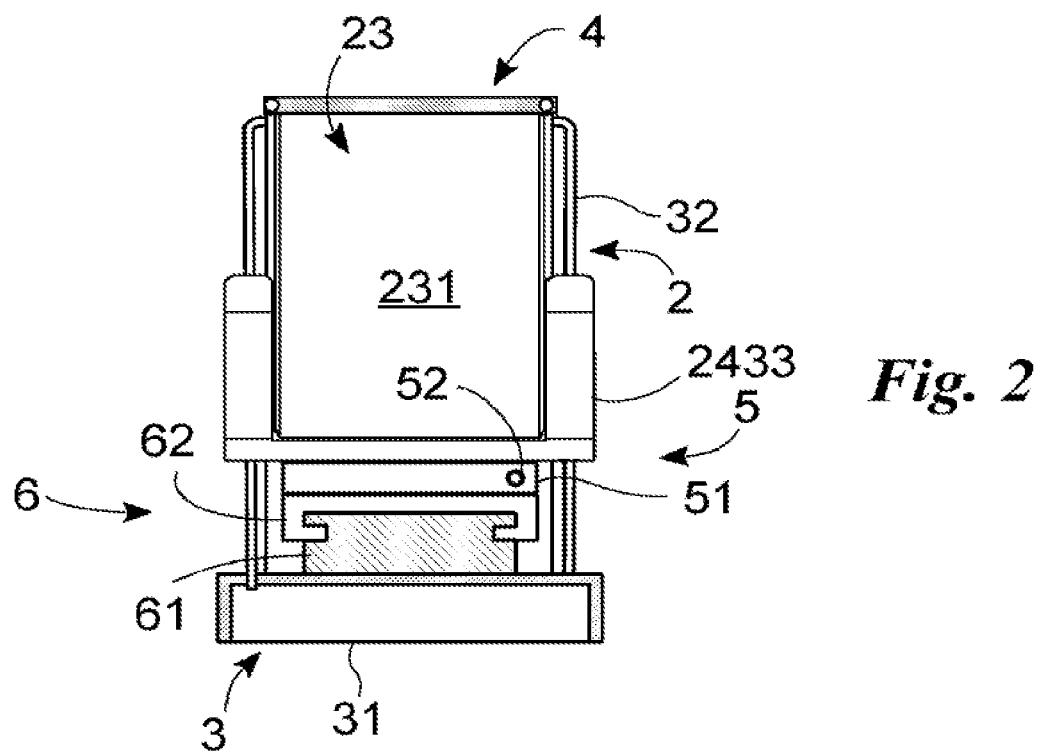
FIG. 2 illustrates, in a front view, a cross-section of the radiological imaging device during the operating sequence shown in FIGS. 1a-1e.

The operator places the patient on the bed 4 and orders the passage into a desired working configuration (FIG. 1d). In particular, the control unit 1a by means of the rotation means 5 rotates the gantry by about 90° thus placing the axes 2c and 4a substantially parallel to each other. Now, the casing 23 and the gantry 2 vary their extension along the circular extension trajectory 2b until the desired angular extension is achieved. During this configuration change, the mobile arched modules 232a and 232b rotate along the circular extension trajectory 2b with opposite rotation directions from each other, placing themselves, in the working configuration of full extension, substantially in contact with each other.

The movements of the first module 232a and of the second module 232b are respectively defined by at least one thrust assembly which initially rotates the bottom module 231 in order to engage the second engagement element 2432 to the mobile guide 242 of the mobile arched modules 232a and 232b. In detail, initially the gantry 2 has the locks stably constraining the mobile arched modules 232a and 232b to the bottom module 231; only the first engagement element 2431 engaged to the bottom guide 241; and the second element 2432 unengaged to the mobile guide 242.

First of all, the unit 1a and, in particular, the thrust assembly 243 drives the first engagement element 2431 so as to rotate the entire casing 23 up to engaging the second element 2432 in one of the sectors and, for example, to the first sector 242b. At this point, the unit 1a orders the first lock to pass into the release configuration, thus undoing the constraint between the first mobile arched module 232a and the bottom arched module 231 and the thrust assembly 243 drives the second element 2431 locking the module 2432. The second element 2432, acting on the mobile guide 242 and, in particular, on the first sector 242b, makes the first mobile arched module 232a come out of the bottom arched module 231. Moreover, such sliding of the first mobile module 232a with respect to the bottom arched module 231 causes the retractable foot 272, initially resting on the first module 232a, to slide along said first module 232a coming, finally to rest on the bottom arched module 231.

Once the portion of the first mobile arched module 232a protruding from the bottom arched module has the desired angular extension, the first lock returns to the locked position and constrains the first mobile arched module 232a to the bottom arched module 231, the thrust assembly 243 drives the first engagement element 2431 so as to rotate, in the opposite direction to the previous, the entire casing 23 as far as engaging the second element 2432 to the second sector 242c. This in the condition in which the second module also needs to protrude from the bottom arched module 231.

At this point, the unit 1a orders the second lock to release the constraint between the second mobile arched module 232b and the bottom arched module 231 and the thrust assembly 243 drives the second element 2431 locking the second element 2432. The second element 2432, acting on the second sector 242c makes the second mobile arched module 232a come out of the bottom arched module 231.

Once the portion of the second mobile arched module 232b protruding from the bottom arched module 231 has the desired angular extension, the unit 1a orders the second lock to constrain the second module 232b to the bottom arched module 231, i.e. to return to the locked position. At this point the radiological imaging device has reached the desired working configuration and can begin scanning.

An appropriate alternative working configuration may be one in which only one of the two modules 232a or 232b protrudes from the bottom arched module 231 so as to guarantee that the source 21 is diametrically opposite the detector 22 and to have a working configuration in which the gantry 2 has an angular extension of less than 360° and thus defines, between its ends of the circular extension trajectory 2b, an access area during scanning. If the source 21 and the detector are not opposite with respect to the central axis 2c, at least one of the supports 27 and 28 moves the source and/or detector 22 until it reaches said position. At this point, the operator selects the type of radiological imaging and the portion of body to analyse. In response to such choice, the control unit 1a defines the position which source 21 and detector 22 must adopt and, as a result, the thrust assembly 243 drives at least one of the of the engagement elements 2431 and/or 2432 so as to rotate the entire casing 23 and move the source 21 and detector 22 into said position. Once the source 21 and detector 22 have reached the desired position, either automatically or in response to a command given by the operator via the control panel 1a, the source 21 and detector 22 perform the radiological imaging.

When the radiological imaging is completed, the operator can perform another scan or, alternatively, order the return of the device 1 to the rest configuration and, thus, perform surgery on the patient without ever moving the patient from the bed 4 of said device.

The disclosed embodiments achieve important advantages. One of the most important advantages is that the imaging device 1, thanks to the possibility of varying the extension of the gantry 2 and thus, placing it under the bed 4, makes it possible to perform a variety of operations/analyses on the patient without removed the same from the bed 4, even for long periods of time, without sacrificing the ability to perform scans from any angle. Therefore, the innovative device allows the operator to leave the patient on the bed at all times without interruption performing on the same site both surgery and radiological scans of various types (X-rays, tomography and fluoroscopy) from all possible angles.

In fact, in the rest configuration, the gantry 2 being almost totally housed in the free chamber 3a, the dimensions of the device 1 are defined exclusively by the bed 4 and by the bearing structure 3 and, therefore, are substantially the same as those of an examination bed, i.e. a bed normally used to move the patient inside a hospital or to perform an operation on the patient. As a result, the device 1 becomes a tool for continuous monitoring of the patient, i.e. able to perform, at any time, imaging of the patient which is utilisable in any part of a hospital (X-ray room, operating theatre, emergency room etc.) while at the same time allowing operations to be performed even in emergencies.

The patient can, moreover, be transported from one place to another without ever leaving the device 1 according to embodiments of the invention. In fact, in the rest configuration, the gantry 2 being almost totally housed in the free chamber 3a, the dimensions of the device 1 are defined exclusively by the bed 4 and by the bearing structure 3. They are substantially the same as those of an examination bed, i.e. a bed normally used to move the patient inside a hospital or to perform an operation on the patient and such as to allow the device 1 to pass through doors, elevators or other openings normally found in a hospital. This aspect is further enhanced by the fact that the imaging device 1, thanks to the innovative gantry 2, does not need to be placed in shielded environments and/or provided with those special conditions characterising radiology rooms currently in use. At the same time the innovative movement apparatus, defining a rotation path of the source and detector of angular amplitude 360° makes it possible to perform scans of 360° degrees or more without interruption.

Another advantage is the fact that the radiological imaging device 1 has high structural simplicity thanks to the possibility of using a single thrust assembly 243 to vary the configuration of the radiological imaging device 1 and to perform the scan.

A further advantage is the ease of assembly and maintenance of the movement apparatus 24. In fact, it is totally outside the casing 23 and therefore easily accessible by an operator.

Another important advantage is determined by the fact that the thrust apparatus 243, thanks to the presence of areas in which the guides 241 mutually overlap, is able to pass gradually from the engagement to the bottom guide 241 to the mobile guide 242 and vice versa. In addition, such smooth transition makes it possible to avoid creating vibrations or other similar noise determining unwanted oscillations of the source 21 and/or of the detector 22, detracting from the quality of the scan.

Another advantage of no less importance is given by the presence of cover blocks 7 which seal the ends of the gantry 2 and prevent the entrance of blood, detritus or other materials that would damage the inner components of the gantry 2.

Another advantage is the fact that the bed 4, thanks to the actuators 33 operable independently of each other, has two degrees of freedom with respect to the structure 3 and the gantry 2. It is in fact both translatable along an axis substantially perpendicular to the support surface 4b and tiltable/rotatable with respect to the central axis 2c.

Variations may be made to the embodiments described herein without departing from the scope of the inventive concept described in the independent claims and in the relative technical equivalents. In said sphere all the details may be replaced with equivalent elements and the materials, shapes and dimensions may be as desired.

The invention claimed is:

1. A radiological imaging device comprising:
a gantry defining an analysis area configured to contain at least a portion of a patient to be analyzed and a circular extension trajectory extending around a central axis, said gantry comprising:
a source configured to emit radiation;
a detector configured to receive said radiation after said radiation has passed through said analysis area; and
a casing defining a housing volume for at least said source and said detector, wherein said casing comprises:
a bottom arched module;
arched modules housed in said bottom arched module, and configured to vary the angular extension of said casing and of said housing volume keeping said source and said detector in said housing volume; and
a movement apparatus, outside said housing volume, configured to move said arched modules to vary extension of said arched modules in opposite rotation directions along a circular trajectory,
wherein the radiological imaging device performs at least two of tomography, fluoroscopy, and X-ray.

2. The radiological imaging device according to claim 1, wherein said gantry further comprises at least one support configured to constrain said source and said detector to said casing and inside said housing volume.

3. The radiological imaging device according to claim 1, wherein said gantry further comprises a first support constraining said source to said bottom arched module and a second support constraining said detector to said mobile arched module.

4. The radiological imaging device according to claim 3, wherein said first support constrains said source to said bottom arched module in a cantilever such that said mobile arched module at least partially comes between said source and said bottom arched module.

5. The radiological imaging device according to claim 4, wherein said first support comprises:
a prop integral with said bottom arched module and configured to support said source cantilevered; and
a retractable foot configured to rest on one of said arched modules and to support said source on the side opposite to said prop.

6. The radiological imaging device according to claim 1, wherein said movement apparatus further comprises:
a bottom guide integral with said bottom arched module and defining a circular movement bottom trajectory substantially centered with respect to said central axis;
a mobile guide integral with said mobile arched module and defining a circular movement mobile trajectory substantially centered with respect to said central axis;
a thrust assembly configured to engage said guides, ordering the rotation of at least part of said arched modules around said central axis to vary the angular extension of said casing; and
at least one through slot made on said bottom arched module and suitable to overlap said mobile guide allowing an engagement between said thrust assembly and said mobile guide when said mobile arched module is inside said bottom arched module.

7. The radiological imaging device according to claim 6, wherein said movement apparatus comprises:
a first engagement element engaged with said bottom guide configured to command the rotation of said bottom arched module; and
a second engagement element engaged with said mobile guide configured to command the rotation of said mobile arched module.

8. The radiological imaging device according to claim 7, wherein said first engagement element and said second engagement element define respectively a first engagement zone and a second engagement zone at least partly overlapping each other radially.

9. The radiological imaging device according to claim 7, wherein said thrust assembly comprises a plurality of said first engagement elements that are mutually angularly spaced along said circular extension trajectory to engage with said bottom guide at distinct points.

10. The radiological imaging device according to claim 9, wherein said first engagement elements have a mutual angular distance substantially between 10° and 30°.

11. The radiological imaging device according to claim 7, wherein said thrust assembly comprises a plurality of said second engagement elements that are mutually angularly spaced along said circular extension trajectory to engage with said mobile guide at distinct points.

12. The radiological imaging device according to claim 11, wherein said second engagement elements have a mutual angular distance substantially between 10° and 30°.

13. The radiological imaging device according to claim 1, wherein said gantry comprises a lock configured to block the relative sliding between said bottom arched module and said mobile arched module defining a locked position that prevents the relative movement between said bottom arched module and said mobile arched module and a release position that allows relative movement between said bottom arched module and said mobile arched module.

14. The radiological imaging device according to claim 13, comprising a control unit configured to command the passage of said lock into its locked position allowing a thrust assembly in said movement apparatus to rotate said gantry around said central axis, and configured to control the passage of said lock into the release position allowing said thrust assembly to reciprocally rotate said bottom arched module and said mobile arched module defining a changed configuration of said gantry.

\* \* \* \* \*